(12) United States Patent
Chiueh et al.

(10) Patent No.: US 11,231,425 B2
(45) Date of Patent: Jan. 25, 2022

(54) IMMUNOASSAY FOR SIMULTANEOUSLY SCREENING ANTI-PLATELET ANTIBODIES AND PERFORMING PLATELETS CROSS MATCHING AND TEST APPARATUS FOR CARRYING OUT SAME

(71) Applicants: Tzong-Shi Chiueh, Taipei (TW); Min-Hsien Wu, Taoyuan (TW); Hsin-Yao Wang, Chiayi (TW)

(72) Inventors: Tzong-Shi Chiueh, Taipei (TW); Min-Hsien Wu, Taoyuan (TW); Hsin-Yao Wang, Chiayi (TW)

(73) Assignees: CHANG GUNG UNIVERSITY, Taoyuan (TW); CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 65 days.

(21) Appl. No.: 16/567,624

(22) Filed: Sep. 11, 2019

(65) Prior Publication Data
US 2020/0110097 A1    Apr. 9, 2020

(30) Foreign Application Priority Data
Oct. 5, 2018 (TW) ................. 107135222

(51) Int. Cl.
*G01N 33/68* (2006.01)
*G01N 33/554* (2006.01)
*G01N 33/569* (2006.01)

(52) U.S. Cl.
CPC ....... *G01N 33/6854* (2013.01); *G01N 33/554* (2013.01); *G01N 33/56977* (2013.01)

(58) Field of Classification Search
None
See application file for complete search history.

(56) References Cited

U.S. PATENT DOCUMENTS 5,110,726 A * 5/1992 Ogden ............... G01N 33/5002
435/2
5,180,661 A * 1/1993 Brubaker ......... G01N 33/56977
435/180

(Continued)

FOREIGN PATENT DOCUMENTS

CN    103336122 B  *  1/2016
CN    108519483 A  *  9/2018

OTHER PUBLICATIONS

Wang et al., Analysis of platelet-reactive alloantibodies and evaluation of cross-match-compatible platelets for the management of patients with transfusion refractoriness, May 2017, British Blood Transfusion Society, 28, 40-46 (Year: 2017).*

(Continued)

*Primary Examiner* — Changhwa J Cheu

(57) ABSTRACT

An immunoassay includes forming first mixtures by reacting a combination reagent with serum of a subject; simultaneously forming second mixtures by reacting randomly selected platelet samples with the serum wherein in each mixture there are immunity compounds formed by combining the platelet antigens with predetermined antibodies in the serum, and other platelet antigens and other antibodies in the serum not forming the immunity compounds; preparing an interception device including receptacles and a filter net; placing each mixture in one receptacle; washing the mixtures wherein the mixtures forming the immunity compounds are intercepted by the filter net with others passing through; adding a signal sensing reagent to each receptacle; reacting the signal sensing reagent with the intercepted mixtures forming the immunity compounds to form final products; and performing a signal sensing to determine (Continued)

whether the final products contain anti-platelet antibodies and determine compatibility of cross matching of respective platelet samples.

5 Claims, 3 Drawing Sheets

(56) References Cited

U.S. PATENT DOCUMENTS

| | | | | |
|---|---|---|---|---|
| 5,514,557 | A | * | 5/1996 | Moghaddam .... G01N 33/56977 435/7.24 |
| 2004/0191891 | A1 | * | 9/2004 | Tsinberg .......... G01N 33/54393 506/9 |
| 2009/0317413 | A1 | * | 12/2009 | Stafford ................ C07K 16/36 424/185.1 |

OTHER PUBLICATIONS

Vun et al., Anti-PF4-heparin immunoglobulin G is the major class of heparin-induced thrombocytopenia antibody: findings of an enzyme-linked immunofiltration assay using membrane-bound hPF4-heparin, Dec. 2001, British Journal of Haematology, 112, 69-75 (Year: 2001).*

Freedman et al., Random Donor Platelet Crossmatching: Comparison of Four Platelet Antibody Detection Methods, 1988, American Journal of Hematology, 28, 1-7 (Year: 1988).*

Xia et al., Establishment of platelet donor registry improves the treatment of platelet transfusion refractoriness in Guangzhou region of China, Jul. 2010, Transfusion Medicine, 20, 269-274 (Year: 2010).*

Wang (Transfus Med Feb. 2018 vol. 28:40-46) (Year: 2018).*

* cited by examiner

IMMUNOASSAY FOR SIMULTANEOUSLY SCREENING ANTI-PLATELET ANTIBODIES AND PERFORMING PLATELETS CROSS MATCHING AND TEST APPARATUS FOR CARRYING OUT SAME

BACKGROUND OF THE INVENTION

1. Field of the Invention

The invention relates to immunoassays for anti-platelet antibodies and more particularly to an immunoassay for simultaneously screening anti-platelet antibodies and performing platelet cross matching and a test apparatus for carrying out the immunoassay.

2. Description of Related Art

Platelets are a component of blood whose function (along with the coagulation factors) is to react to bleeding from blood vessel injury by clumping, thereby initiating a blood clot. Platelets have no cell nucleus: they are fragments of cytoplasm that are derived from the megakaryocytes of the bone marrow, and then enter the circulation. Circulating unactivated platelets are biconvex discoid structures, 2-4 μm in greatest diameter.

On the surfaces of platelets, there are Class I HLA (human leukocyte antigen) and various cell membrane protein molecules for initiating a blood clot. There are differences between them in different bodies, i.e., being different in antigens. Thus, platelets transfused from a different body may sensitize patients and then induce production of anti-platelet antibodies. Regarding the various cell membrane protein molecules for initiating a blood clot, they are classified as HPA (human platelet antigen)-1 to HPA-28 in which HPA3/1, 4, and 6 are on the IIb(CD41)/IIIa(CD61) complex, and HPA-5 is on the Ia/IIa complex.

Currently, analytical biochemistry assays for anti-platelet antibodies fall into the following three assays. The first assay is to attach platelets to a surface. The second assay is enzyme linked immunosorbent assay (ELISA). The third assay is LUMINEX™ immunoassay which covers Pak-L of purified platelet antigens used by IMMUCOR™.

Regarding the first assay of attaching platelets to a surface, it can be a solid phase red cell adherence test (SPRCA) or a monoclonal antibody solid-phase platelet antibody test (MASPAT). Both use limited, randomly selected platelets as antigen reagents for test. Thus, these platelet antigens are not sufficient to test some anti-platelet antibodies. Also, the randomly selected platelets render a verification of the test results impossible. Further, SPRCA uses labeled red cells as the final reaction index and it may greatly decrease sensitivity because of problems of keeping the red cells in good conditions. Finally, MASPAT has drawbacks including tedious test steps, poor timing, and being impossible of finishing test prior to issuing platelet.

Regarding ELISA, it can be a monoclonal antibody immobilization of platelet antigens assay (MAIPA) or Pak-Plus assay used by IMMUCOR™. This kind of ELISA uses purified platelet antigens protein and Class I HLA protein to categorize anti-platelet antibodies as anti-HLA or anti-HPA. However, it cannot perform a platelet cross matching assay.

The third assay, LUMINEX™ immunoassay, uses purified platelet antigen molecules and is particularly suitable for testing anti-HLA or anti-HPA antibodies. However, it still cannot perform a platelet cross matching assay.

Currently, in the verification of anti-platelet antibodies, a blood bank may not have a sufficient number of platelets if using randomly selected platelets as antigen reagents for SPRCA. Also, it is impossible to ascertain antigen coverage even there are sufficient platelets. In case of using MASPAT reagents manufactured by Sanquin, platelet antigens of foreigners are not applicable to distribution frequency of antigens of Chinese. Both may render test results of pseudo negative of anti-platelet antibodies. Also, antigen reagents of platelet are not easy to attach to a surface and are subject to reeling in the washing step after immunoassay. MAIPA and Pak-Plus of ELISA cannot be used for platelets cross matching tests. Regarding using SPRCA or MASPAT to do screening and cross matching test, it is impossible to finish testing prior to issuing platelet units.

Thus, the need for improvement still exists.

SUMMARY OF THE INVENTION

It is therefore one object of the invention to provide an immunoassay for simultaneously screening anti-platelet antibodies and performing platelet cross matching, comprising the steps of forming a plurality of first mixtures by reacting a combination reagent of a plurality of different platelet antigens with serum of a subject; simultaneously forming a plurality of second mixtures by reacting a plurality of randomly selected samples from platelet units with the serum of the subject wherein in each of the first and second mixtures there are a plurality of immunity compounds formed by combining the platelet antigens with predetermined antibodies in the serum of the subject, and other platelet antigens and other antibodies in the serum of the subject not forming the immunity compounds; preparing an interception device including a plurality of receptacles and a filter net with the receptacles placed thereon, the filter net having a plurality of apertures having a size less than 4.0 μm; placing each of the first and second mixtures in one of the receptacles; washing the first and second mixtures wherein the first and second mixtures forming the immunity compounds are intercepted by the filter net and the other antibodies in the serum of the subject not forming the immunity compounds pass through the filter net; adding at least one signal sensing reagent to each of the receptacles; reacting the signal sensing reagent with the intercepted first and second mixtures forming the immunity compounds to form a plurality of final products; and performing a signal sensing to determine whether the final products contain anti-platelet antibodies and further determine compatibility of cross matching of respective platelet samples.

The invention has the following advantages and benefits in comparison with the conventional art:

It can test a substantial portion of anti-platelet antibodies by selecting an optimum combination of different platelet antigens, mixing same to form a combination reagent of platelet antigens, and carrying out the immunoassay by means of the combination reagent of platelet antigens.

It can increase test results recurrence by intercepting the immunity compounds performed by the interception device after the washing step in which the immunity compounds are formed by combining the platelet antigens with predetermined antibodies in the serum.

The immunoassay is carried out to simultaneously screen anti-platelet antibodies and perform platelet cross matching. The immunoassay can verify the platelet samples prior to issuing platelet units. The quick immunoassay can greatly lower the risk of a patient having continuous low platelets in addition to saving the precious platelet samples.

The above and other objects, features and advantages of the invention will become apparent from the following detailed description taken with the accompanying drawings.

DETAILED DESCRIPTION OF THE INVENTION

Figure 1:
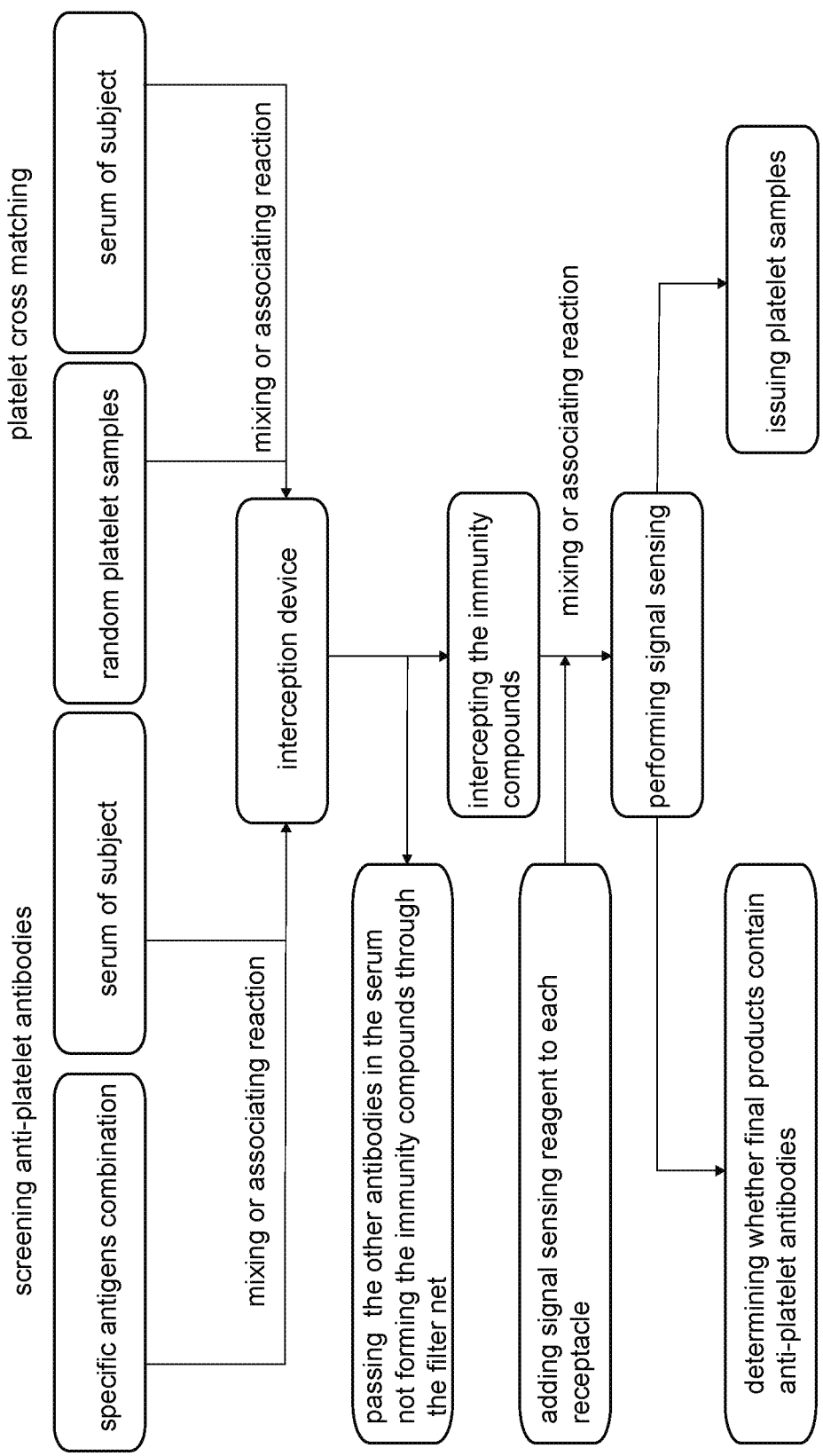
FIG. 1 is a flow chart illustrating an immunoassay for simultaneously screening anti-platelet antibodies and performing platelets cross matching according to the invention.
Figure 2:
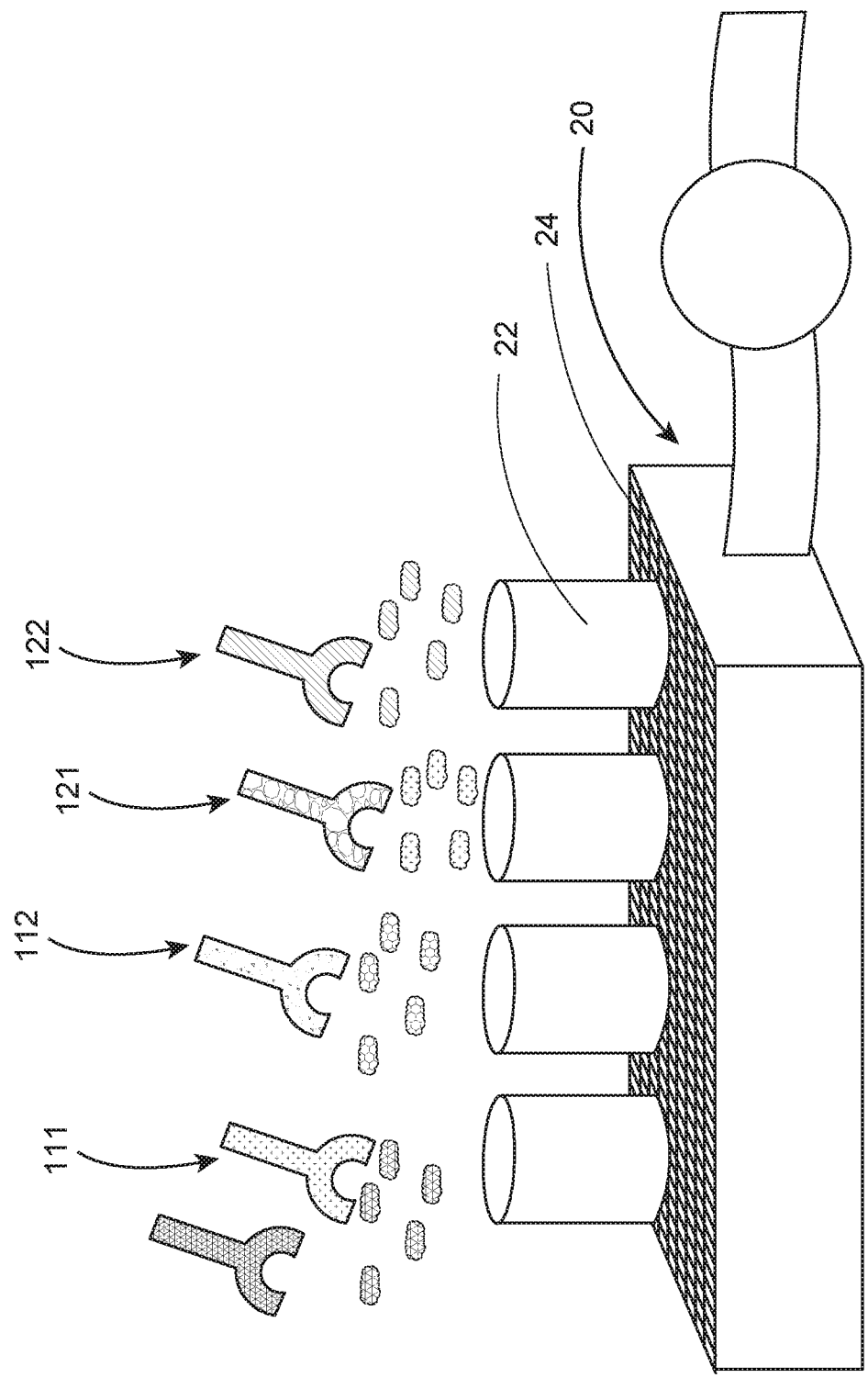
FIG. 2 schematically depicts forming a plurality of first mixtures by reacting a combination reagent of a plurality of different platelet antigens with serum of a subject, and simultaneously forming a plurality of second mixtures by reacting a plurality of randomly selected platelet samples with the serum of the subject according to the invention.

Referring to FIGS. 1 and 2, a flow char of an immunoassay for simultaneously screening anti-platelet antibodies and performing platelets cross matching according to the invention is illustrated. The immunoassay comprises the following steps:

Forming a plurality of first mixtures 111 and 112 by reacting a combination reagent of a plurality of different platelet antigens with serum of a subject, and simultaneously forming a plurality of second mixtures 121 and 122 by reacting a plurality of randomly selected platelet samples with the serum of the subject. In each of the first and second mixtures 111, 112, 121 and 122, a plurality of immunity compounds are formed by combining the platelet antigens with specific antibodies in the serum, and other platelet antigens and other antibodies in the serum of the subject not forming the immunity compounds.

The combination reagent is platelets, platelet fragments, tiny particles attached to the platelet antigens, or any combination thereof. The reaction means that antibodies in the serum react with antigens of platelets. In the invention, the combination reagent is 0 type platelets. The different platelet antigens are a combination of human leukocyte antigens (HLA), human platelet antigens (HPA), and glycoprotein (e.g., Ia, Ibα, Ibβ, IIa, IIb, IIIa, IX, and CD109). The combination reagent is tested on Taiwan Han Chinese, Taiwan Minnan and Taiwan Hakka based on distribution frequency of racial group gene type as shown in the following tables 1, 2 and 3. In the tables 1, 2 and 3, a combination reagent having platelets with representative antigens is selected in order to correctly examine types of anti-platelet antibodies being frequently found in these three racial groups.

TABLE 1

Distribution frequency of HLA-A in Taiwan

| Ranking | 2-digit Allele | subpopulation | Freq |
|---|---|---|---|
| 1 | A*11 | Taiwan Han Chinese | 0.326 |
| 2 | A*02 | Taiwan Han Chinese | 0.268 |
| 3 | A*24 | Taiwan Han Chinese | 0.158 |

TABLE 1-continued

Distribution frequency of HLA-A in Taiwan

| Ranking | 2-digit Allele | subpopulation | Freq |
|---|---|---|---|
| 4 | A*33 | Taiwan Han Chinese | 0.118 |
|   | A*31 | Taiwan Han Chinese | 0.028 |
|   | A*02 | Taiwan Han Chinese | 0.027 |
|   | A*26 | Taiwan Han Chinese | 0.024 |
|   | A*30 | Taiwan Han Chinese | 0.012 |
| 1 | A*11 | Taiwan Minnan | 0.349 |
| 2 | A*02 | Taiwan Minnan | 0.317 |
| 3 | A*24 | Taiwan Minnan | 0.166 |
| 4 | A*33 | Taiwan Minnan | 0.116 |
|   | A*26 | Taiwan Minnan | 0.013 |
|   | A*30 | Taiwan Minnan | 0.012 |
|   | A*31 | Taiwan Minnan | 0.012 |
| 1 | A*11 | Taiwan Hakka | 0.361 |
| 2 | A*02 | Taiwan Hakka | 0.316 |
| 3 | A*24 | Taiwan Hakka | 0.17 |
| 4 | A*33 | Taiwan Hakka | 0.104 |
|   | A*30 | Taiwan Hakka | 0.016 |
|   | A*26 | Taiwan Hakka | 0.013 |

TABLE 2

Distribution frequency of HLA-B in Taiwan

| Ranking | 2-digit Allele | subpopulation | Freq |
|---|---|---|---|
| 1 | B*40 | Taiwan Han Chinese | 0.211 |
| 2 | B*46 | Taiwan Han Chinese | 0.136 |
| 3 | B*58 | Taiwan Han Chinese | 0.106 |
| 4 | B*13 | Taiwan Han Chinese | 0.056 |
| 5 | B*15 | Taiwan Han Chinese | 0.045 |
| 6 | B*51 | Taiwan Han Chinese | 0.044 |
|   | B*54 | Taiwan Han Chinese | 0.042 |
|   | B*55 | Taiwan Han Chinese | 0.035 |
|   | B*38 | Taiwan Han Chinese | 0.033 |
|   | B*15 | Taiwan Han Chinese | 0.026 |
|   | B*27 | Taiwan Han Chinese | 0.026 |
|   | B*39 | Taiwan Han Chinese | 0.025 |
| 1 | B*40 | Taiwan Minnan | 0.242 |
| 2 | B*46 | Taiwan Minnan | 0.146 |
| 5 | B*15 | Taiwan Minnan | 0.131 |
| 3 | B*58 | Taiwan Minnan | 0.107 |
| 4 | B*13 | Taiwan Minnan | 0.083 |
| 6 | B*51 | Taiwan Minnan | 0.06 |
|   | B*38 | Taiwan Minnan | 0.037 |
|   | B*55 | Taiwan Minnan | 0.03 |
|   | B*27 | Taiwan Minnan | 0.027 |
|   | B*39 | Taiwan Minnan | 0.026 |
|   | B*54 | Taiwan Minnan | 0.025 |
|   | B*35 | Taiwan Minnan | 0.015 |
|   | B*48 | Taiwan Minnan | 0.012 |
| 1 | B*40 | Taiwan Hakka | 0.25 |
| 2 | B*46 | Taiwan Hakka | 0.156 |
| 5 | B*15 | Taiwan Hakka | 0.147 |
| ### | B*35 | Taiwan Hakka | 0.14 |
| 3 | B*58 | Taiwan Hakka | 0.101 |
| 4 | B*13 | Taiwan Hakka | 0.087 |
| 6 | B*51 | Taiwan Hakka | 0.056 |
|   | B*38 | Taiwan Hakka | 0.038 |
|   | B*55 | Taiwan Hakka | 0.031 |
|   | B*39 | Taiwan Hakka | 0.028 |
|   | B*27 | Taiwan Hakka | 0.025 |
|   | B*54 | Taiwan Hakka | 0.016 |

TABLE 3

Distribution frequency of HLA in Taiwan

| | Frequency major allele (%) | Heterozygosity (%) | Mismatch platelet transfusion (%) |
|---|---|---|---|
| HPA-1 | 99.55 | 0.90 | 0.89 |
| HPA-2 | 96.49 | 6.61 | 6.54 |
| HPA-3 | 55.81 | 52.30 | 37.16 |
| HPA-4 | 99.75 | 0.50 | 0.50 |
| HPA-5 | 98.50 | 2.96 | 2.92 |
| HPA-6 | 97.75 | 4.41 | 4.31 |
| HPA-15 | 53.71 | 49.73 | 37.76 |

Figure 3:
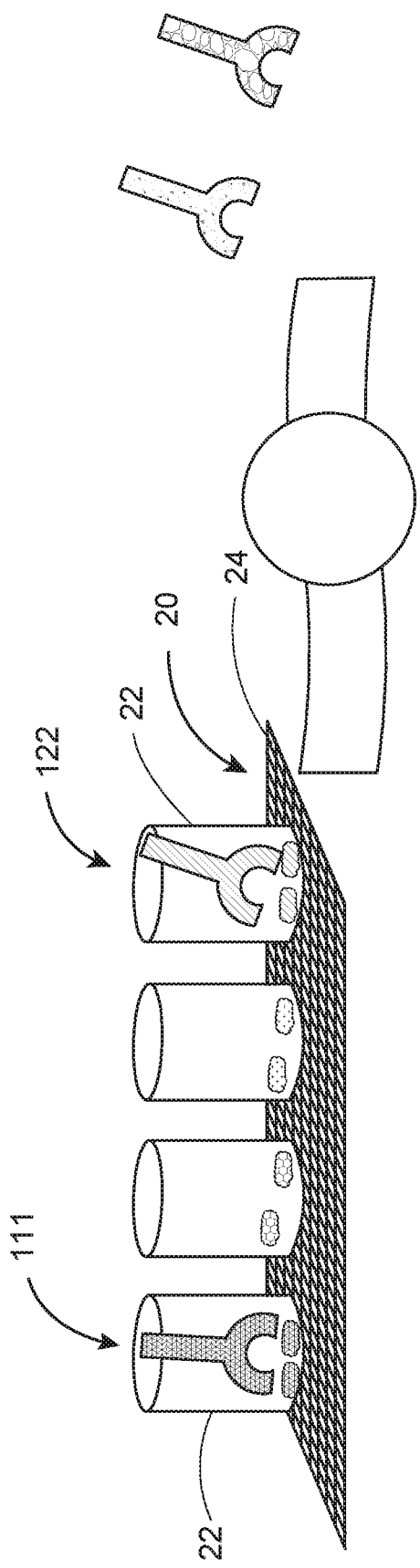
FIG. 3 is a view similar to FIG. 2 schematically depicts intercepting immunity compounds of the platelet antigens and the serum formed by the first and second mixtures by means of a interception device according to the invention.

Referring to FIGS. 2 and 3 in conjunction with FIG. 1, an interception device 20 is shown and the interception device 20 comprises a plurality of receptacles 22 and a filter net 24 with the receptacles 22 placed thereon, the filter net 24 having a plurality of apertures with a size less than 4.0 μm. Each of the first and second mixtures 111, 112, 121 and 122 is placed in one of the receptacles 22. Further, the first mixtures 111 and 112 and the second mixtures 121 and 122 are washed in which the first mixture 111 and the second mixture 122 forming the immunity compounds are intercepted by the filter net 24 and the other antibodies in the serum not forming the immunity compounds pass through the filter net 24. The washing can be implemented by gravitational penetration, capillary action, vacuum suction or plunger pressing.

Figure 4:
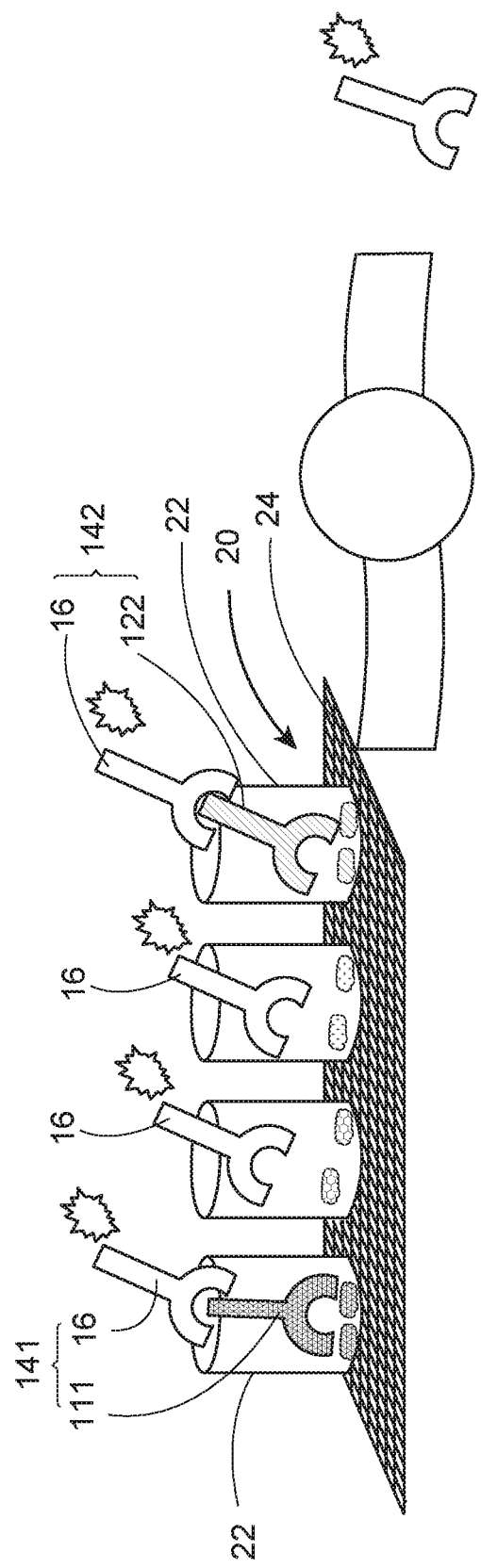
FIG. 4 is a view similar to FIG. 3 schematically depicts adding a plurality of signal sensing reagents to the immunity compounds for reaction to form final products according to the invention.

Referring to FIG. 4 in conjunction with FIG. 1, at least one signal sensing reagent 16 is added to each receptacle 22. The signal sensing reagent 16 reacts with the intercepted first mixture 111 and second mixture 122 forming the immunity compounds to form final products 141 and 142. The signal sensing reagent 16 is immunoglobulin, avidin, biotin or a portion thereof. Finally, a signal sensing is performed. It is possible to determine whether the final products 141 and 142 contain anti-platelet antibodies and to further determine compatibility of cross matching of respective platelet samples by sensing visible light, electroluminescent, fluorescent, or electromagnetic signals emitted by the final products 141 and 142.

Subsequently, cross matching is performed on the subject. In the test, both negative quality controls (QCs) and positive QCs are taken as control group in which negative QCs are taken from serum of a subject not transferring blood to himself or herself and confirmed by MASPAT, and positive QCs are taken from anti-platelet antibodies anti-CD41 having known consistence. The anti-platelet antibodies anti-CD41 is reacted with combination reagent of different platelet antigens for immunoassay and subsequent interception, washing and signal sensing steps.

In the cross matching of table 4, QCs of types 1, 2 and 3 are invalid and re-assay is required for each type.

Regarding type 4, the antibody screening shows negative and the cross matching shows negative, i.e., no anti-platelet antibodies. Thus, in the type 4, the platelets (1) to (n) in the cross matching are suitable for transfusion.

Regarding type 5, the antibody screening shows negative and the cross matching shows positive in the platelet (2) and negative in the remaining platelets. Thus, in the type 5, except the platelet (2), the remaining platelets in the cross matching are suitable for transfusion.

Regarding type 6, the antibody screening shows positive and the cross matching shows negative in each of the platelets (1) and (2) and positive in each of the remaining platelets. Thus, in the type 6, the platelets (1) and (2) in the cross matching are suitable for transfusion.

Regarding type 7, the antibody screening shows positive and the cross matching shows positive in each of the platelets (1) to (n). Thus, the platelets (1) to (n) and the type 7 are not suitable. It is required to select other platelets for cross matching or platelets compatible for HLA.

Regarding type 8, the antibody screening shows positive and the cross matching shows negative in each of the platelets (1) to (n). Thus, re-assay is required for the type 8.

TABLE 4 cross matching assay results and explanations

| Type | Negative QC | Positive QC | Antibody screening | Cross matching (1) | Cross matching (2) | Cross matching (3) | Cross matching (4) | Cross matching (n) | result |
|---|---|---|---|---|---|---|---|---|---|
| 1 | N | N | N or P | N or P | N or P | N or P | N or P | N or P | Invalid QC and re-assay required |
| 2 | P | P | N or P | N or P | N or P | N or P | N or P | N or P | Invalid QC and re-assay required |
| 3 | P | N | N or P | N or P | N or P | N or P | N or P | N or P | Invalid QC and re-assay required |
| 4 | N | P | N | N | N | N | N | N | No anti-platelet antibodies, number(1)-(n) platelet suitable for transfusion |
| 5 | N | P | N | N | P | N | N | N | Low frequency anti-platelet antibodies exist, number(2) platelet not suitable, other numbered platelet suitable for transfusion |
| 6 | N | P | P | N | N | P | P | P | Positive anti-platelet antibodies, number(1), (2) platelet suitable for transfusion |
| 7 | N | P | P | P | P | P | P | P | Positive anti-platelet antibodies, random n platelets not suitable, other platelets required for cross matching or selecting HLA compatible platelets |
| 8 | N | P | P | N | N | N | N | N | Having anti-platelet antibodies, compatible with randomly selected n platelets, re-assay required |

N: negative reaction
P: positive reaction

The invention further provides an immunoassay for simultaneously screening anti-platelet antibodies and performing platelet cross matching and a test apparatus for carrying out the immunoassay. The test apparatus is implemented as an interception device 20 comprising a plurality of receptacles 22 and a filter net 24 with the receptacles 22 placed thereon, the filter net 24 having a plurality of apertures having a size less than 4.0 µm.

Preferably, the apertures of the filter net 24 have a size between 0.2-3.0 µm.

Preferably, the filter net 24 of the interception device 20 is formed of polyvinylidene difluoride (PVDF), nitrocellulose, polytetrafluoroethylene (PTFE), nylon film (e.g., nylon polyamide (PA) fiber), polyether sulfones (PES), cellulose acetate, mixed cellulose ester (MCE), aqueous gels or paper fiber.

While the invention has been described in terms of preferred embodiments, those skilled in the art will recognize that the invention can be practiced with modifications within the spirit and scope of the appended claims.

What is claimed is:

1. An immunoassay for simultaneously screening anti-platelet antibodies and performing platelet cross matching, comprising the steps of:
    forming a plurality of first mixtures b reacting a combination reagent of a plurality of different platelet antigens with a first portion of a serum sample from a subject;
    simultaneously forming a plurality of second mixtures by reacting a plurality of randomly selected platelet samples with a second portion of the serum sample from the subject;
    wherein in each of the first and second mixtures there are a plurality of immunity compounds formed by combining the platelet antigens with the anti-platelet antibodies in the serum of the subject, and other platelet antigens and other antibodies in the serum of the subject not forming the immunity compounds;
    preparing an interception device including a plurality of receptacles and a filter net with the receptacles placed thereon, the filter net having a plurality of apertures having a size less than 4.0 µm;
    placing each of the first and second mixtures in one of the receptacles;
    washing the first and second mixtures wherein the first and second mixtures forming the immunity compounds are intercepted by the filter net and the other antibodies and the other platelet antigens in the serum of the subject not forming the immunity compounds pass through the filter net;
    adding at least one signal sensing reagent to each of the receptacles;
    reacting the signal sensing reagent with the intercepted first and second mixtures forming the immunity compounds to form a plurality of final products; and
    performing a signal sensing to determine both whether the final products contain anti-platelet antibodies and further simultaneously determine compatibility of cross matching of respective platelet samples,
    wherein the washing is implemented by gravitational penetration, capillary action, vacuum suction or plunger pressing.

2. The immunoassay of claim 1, wherein the combination reagent is selected based on distribution frequency of racial group gene type, and the racial group gene type is a combination of human leukocyte antigens (HLA) and human platelet antigens (HPA).

3. The immunoassay of claim 1, wherein the combination reagent is platelets, platelet fragments, tiny particles attached to the platelet antigens, or any combination thereof.

4. The immunoassay of claim 1, wherein the signal sensing reagent is immunoglobulin, avidin, biotin or a portion thereof.

5. The immunoassay of claim 1, wherein signals emitted by the final products are visible light, electroluminescent, fluorescent or electromagnetic signals.

* * * * *